US009040283B2

(12) United States Patent
Muller-Feuga (10) Patent No.: US 9,040,283 B2
(45) Date of Patent: May 26, 2015

(54) PHOTOSYNTHETIC REACTOR FOR CULTIVATING MICROORGANISMS, AND METHOD FOR CULTIVATING MICROORGANISMS

(75) Inventor: Arnaud Muller-Feuga, Baillargues (FR)

(73) Assignee: MICROPHYT (FR)

( * ) Notice: Subject to any disclaimer, the term of this patent is extended or adjusted under 35 U.S.C. 154(b) by 634 days.

(21) Appl. No.: 13/256,544

(22) PCT Filed: Mar. 9, 2010

(86) PCT No.: PCT/FR2010/050395
§ 371 (c)(1),
(2), (4) Date: Oct. 10, 2011

(87) PCT Pub. No.: WO2010/109108
PCT Pub. Date: Sep. 30, 2010

(65) Prior Publication Data
US 2012/0021498 A1    Jan. 26, 2012

(30) Foreign Application Priority Data
Mar. 25, 2009   (FR) ..................................... 09 51917

(51) Int. Cl.
*C12M 1/00*       (2006.01)
*C12M 1/12*       (2006.01)

(52) U.S. Cl.
CPC ............... *C12M 29/00* (2013.01); *C12M 21/02* (2013.01); *C12M 23/06* (2013.01); *C12M 39/00* (2013.01)

(58) Field of Classification Search
CPC ...... C12M 21/02; C12M 39/00; C12M 29/00; C12M 23/06
See application file for complete search history.

(56) References Cited

U.S. PATENT DOCUMENTS 4,122,575 A * 10/1978 Sagawa ..................... 15/104.061
6,602,703 B2 * 8/2003 Dutil ......................... 435/292.1
(Continued)

FOREIGN PATENT DOCUMENTS

EP    1925660 A1    5/2008
ES    2150389 A1    11/2000
(Continued)

OTHER PUBLICATIONS

International Search Report issued Aug. 18, 2010 by European Patent Office re: International Application No. PCT/FR2010/050395; citing: Muller-Fuega et al., FR 2 685 344 A, FR 2 914 315 A, US 2007/231886 A1 and EP 1 925 660 A.
(Continued)

*Primary Examiner* — Nathan Bowers
*Assistant Examiner* — Gautam Prakash
(74) *Attorney, Agent, or Firm* — Cantor Colburn LLP (57)   ABSTRACT

A photosynthetic reactor (1) suitable for cultivating photosynthetic microorganisms, notably algae, comprising at least one photosynthetic reaction pipe (2) at least one return pipe (3), at least one means (4) for circulating the liquid culture medium, at least one gas injection means (5) and at least one exhaust means (6) positioned in the high portion of the reactor (1), wherein the placement of the gas injection means (5) and/or the conformation of the reaction pipe (2) or of the return pipe (3) are designed so that the gas injected by the injection means (5) rises again to the exhaust means (6) by circulating in the reaction pipe (2), in a low-to-high flow direction, so that the injected gas and the liquid culture medium establish a gas/liquid two-phase flow in a substantially horizontal reaction section (23) of the reaction channel (2).

The present invention finds application in the field of cultivating photosynthetic microorganisms and notably algae.

24 Claims, 6 Drawing Sheets

(56) References Cited

U.S. PATENT DOCUMENTS

2002/0072109 A1    6/2002    Bayless et al.
2007/0231886 A1    10/2007    Kahlert et al.

FOREIGN PATENT DOCUMENTS

| | | |
|---|---|---|
| ES | 2193860 A1 | 11/2003 |
| FR | 2685344 A1 | 6/1993 |
| FR | 2914315 A1 | 10/2008 |
| GB | 2118572 A | 11/1983 |
| GB | 2331762 A | 6/1999 |

OTHER PUBLICATIONS

J.C. Merchuk et al. "Fluid flow and mass transfer in a counter-current gas-liquid inclined tubes photo-bioreactor", Chemical Engineering Science; 2007; vol. 62; pp. 7414-7425.

Douglas J. Reinemann et al. "Two-Phase Cleaning Flow Dynamics in Air Injected Milklines" Transactions of the ASAE; 1994; vol. 37; No. 5; pp. 1531-1536.

A. Muller-Feuga et al. "Swirling Flow Implementation in a Photobioreactor for Batch and Continuous Cultures of Porphyridium cruentum", Biotechnology and Bioengineering, Dec. 5, 2003, pp. 544-551, vol. 84, No. 5, Wiley & Sons, Hoboken NJ, USA.

\* cited by examiner

PHOTOSYNTHETIC REACTOR FOR CULTIVATING MICROORGANISMS, AND METHOD FOR CULTIVATING MICROORGANISMS

CROSS REFERENCE TO RELATED APPLICATIONS

This is a U.S. national stage of application No. PCT/FR2010/050395, filed on Mar. 9, 2010, which claims priority of French application Ser. No. 09/51917, filed on Mar. 25, 2009.

TECHNICAL FIELD

The present invention relates to a photosynthetic reactor suitable for cultivating photosynthetic microorganisms, notably algae, and also to a method for cultivating photosynthetic microorganisms using such a reactor.

More particularly it relates to a photosynthetic reactor comprising:

at least one photosynthetic reaction pipe in which the liquid culture medium circulates and which is provided with at least one substantially horizontal reaction section and made at least partly in a material transparent to solar radiation, said pipe having a low end positioned in the low portion of the reactor and a high end positioned in the high portion of the reactor above the low end;

at least one return pipe ensuring the fluidic connection between the low end and the high end of the reaction pipe; and at least one means for circulating the liquid culture medium.

The present invention applies to the culture of any photosynthetic organism, i.e. any life form capable of development and of photosynthesis in a suitable nutritive culture medium, in the presence of solar radiation and of a carbon-rich gas such as carbon dioxide.

BACKGROUND

Among photosynthetic microorganisms concerned by the invention are more particularly represented aquatic plants such as for example micro-algae, moss protonemas, small macro-algae and isolated cells of multicellular plants. These aquatic plants have interesting properties in the fields, notably of pharmacy, human and animal nutrition, of dermo-cosmetology, of energy and of the environment.

Like for most photosynthetic microorganisms, access to this resource essentially consists in assisted culture in suitable reactors. As light is their main substrate, the culture medium should have an optical interface receiving a light flux. The difficulty of cultivating photosynthetic microorganisms lies in the fact that they themselves form obstacles to the passage of light, which is their main substrate. The growth of the culture will therefore stabilize when light no longer penetrates into the thickness of the culture. This phenomenon is called self-shadowing.

The length of the optical path or "light path length", allows characterization of the different confinement modes and is defined as being:

the length of the light path from its entry into the culture through a transparent optical interface to as far as an opposite opaque wall; or the half of the distance separating both transparent optical interfaces when the confinement receives light through two opposite transparent optical interfaces.

This optical path length varies between a few centimeters and a few decimeters and essentially determines the propipeion of biomass per unit time and per optical unit surface (surface propipeivity in $g/m^2/d$) and the concentration of the culture between (in g/L) in the final growth phase. The various confinement modes which are applied for ensuring the culture of small aquatic plants may thus be classified according to this characteristic length.

The photosynthesis reaction is also accompanied by consumption of carbon dioxide ($CO_2$) and by propipeion of oxygen ($O_2$). Excess oxygen inhibits the reaction, while the absence of carbon dioxide interrupts it through lack of substrate to be transformed. A gas/liquid interface should therefore be placed for mass transfers between these gases and the liquid phase. In order to promote these exchanges and to avoid heterogeneities, the culture should be the centre of a mixture intended to renew the organisms at the aforementioned optical interface and also at this gas/liquid interface.

A first known embodiment of a photosynthetic reactor consists in an open container of the basin or tank type where the culture is maintained by gravity and has a free surface achieving by itself the optical interface and the liquid/gas interface. The culture is mixed inside the basin by one or more mechanical stirring devices, for example of the paddle wheel type. The thereby achieved basin cultures may cover significant surface areas and this embodiment is at the origin of the essential of the present world propipeion of micro-algae, which attains several thousand metric tons of dry weight. Photosynthetic organisms produced by this type of reactor are essentially:

so-called extremophilic algae, the media of which are hostile to predators and competitors, such as for example algae of the spirulin or *Dunaliella* type; or so-called dominating algae, which withstand mechanical stresses or contaminations better than the other ones, such as for example the algae of the *Chlorella, Scenedesmus, Skeletonema, Odontella* or *Nannochloropsis* type.

A second known embodiment of a photosynthetic reactor also consists in an open container of the reservoir or tank type, but the dimensions of which are smaller than that of the basins of the first known embodiment. These containers generally have lateral walls transparent to solar radiation, so that the optical interface is formed both by the free surface of the liquid medium and by the transparent lateral walls.

In this second embodiment, it is conventional to resort to injection of air carried out in the low portion of the reservoir which leads to the formation of air bubbles moving up in the liquid to the free surface. The surface of the thereby formed bubbles is the gas/liquid interface. By moving up to the surface, the bubbles carry away the culture upwards, thereby generating convective motions which may extend to the whole volume. Carbon dioxide ($CO_2$) is sometimes added to the injected air in order to provide extra carbon according to a predefined molar fraction of a few percent.

With a volume of less than that of the basins of the first embodiment, the reservoirs of the second known embodiment are adapted to more controlled cultures, in particular to the cultures of micro-algae intended for feeding larvae of molluscs or living preys of fish larvae in aquaculture. Frequent cleaning of these reservoirs as well as pure and bulk inoculations allow limitation of the contaminations inside the reservoir. With a number of several tens of species, the thereby cultivated micro-algae have temperature and light needs relatively close which makes their culture possible in premises common thereto.

Both of these embodiments in the form of an open container provide an optical path length from one to several decimeters.

A third known embodiment of a photosynthetic reactor consists in a closed reactor, a so-called photobioreactor and which comprises a closed mouth inside which the liquid culture medium circulates, said closed loop comprising a reaction pipe provided with reaction sections made in a material transparent to the light radiation (or to light), and a return pipe ensuring the connection between both opposite ends of the reaction pipe.

The photobioreactors, notably described in documents GB 2,118,572 A, ES 2 193 860 A1, GB 2,331,762 A, ES 2 150 389 A1, FR 2 685 344 A1 and FR 2 875 511 A3, provide substantially smaller optical path lengths, of the order of one to several centimeters, as compared with the embodiments with an open container, and they give the possibility of attaining concentrations of photosynthetic organisms of several g/L sheltered from aerial contaminations. The reaction pipe of photobioreactors generally consists in transparent plates or tubes, in glass or plastic, with a thickness and a diameter of the order of 1 cm, which are connected end to end through bends in order to form together a pipe in the form of a coil.

The return pipe comprises a so-called ascending vertical tube in which the liquid medium moves upwards, and a descending vertical tube in which the liquid medium moves down under the effect of gravity.

The gas injection system generally applied in photobioreactors consists in a gas siphon, otherwise called a "gas-lift" or a gas lifting device, i.e. in an injection of gas at the base of the ascending vertical tube of the return pipe; said gas injection being used both for circulating or displacing the liquid reaction medium and for achieving gas-liquid exchanges. The gas lift includes in its high portion a reservoir with a load or widened volume wherein the lower circulation rates allow gas-liquid separation, and the descending vertical tube of the return pipe opens out in the bottom of the load reservoir for feeding the reaction pipe with liquid.

The aforementioned photobioreactors apply the principle according to which the reaction only occurs in the liquid phase, in other words these photobioreactors seek to minimize the volume of injected gas into the reactor so as not to reduce the volume of the liquid culture medium by as much, with the concern of not reducing propipeion. Thus, in these photobioreactors, extraction of oxygen is achieved by means of the vertical ascending tube defined above; said vertical ascending tube forming a column of air bubbles opening out into the load reservoir receiving the liquid culture medium, and including injection of gas in the low portion, opportunely $CO_2$-enriched air. As described above, both circulation and gas transfer functions coincide within this single device called a gas lift, which generates an ascending vertical circulation by exchange of momentum between the liquid mass and the gas bubbles resulting from the injection. The photosynthetic oxygen in oversaturation in the liquid passes into the gas phase by sweeping with air, while $CO_2$ passes into solution. These degassing and carbonation functions are indispensable and occur at this single device simultaneously.

The gas lifts have the drawback of generating gas bubbles which move up the vertical ascending tube of the return pipe of the photobioreactors. The applicant has actually observed the deleterious role of these bubbles for cultivating microorganisms in photobioreactors:

the bubbles mechanically stress the micro-algae and may be detrimental to fragile microorganisms on the one hand; and the bubbles capture by a surfactant effect the molecules which have surfactant properties, and notably organic molecules, cell debris and excretion propipes of living cells on the other hand.

These substances normally dispersed in the medium in the absence of bubbles are thus gathered as aggregates at the free surface of the load reservoir when the bubbles burst. The bacteria and fungi which could not develop because of the strong dilution of these organic molecules then find concentrated substrates favorable to their development.

One of the goals of the present invention is to avoid or at least limit the formation of bubbles in order to:

contain the bacterial and fungal development for example in order to remain compatible with conventionally imposed sanitary standards in the culture of microorganisms; and limit the mechanical stresses in the liquid culture medium, and thereby allow the cultivation of certain fragile microorganisms which were up to now excluded from such cultivation in a reactor.

In an alternative embodiment of the gas lift, deoxygenation of the liquid culture medium circulating in the photobioreactor is obtained by causing the liquid medium to gravitationally fall into a container with a constant level. The liquid culture medium is here circulated by a pumping means, notably of the centrifugal pump type, positioned in the reaction pipe designed for not only compensating for the pressure losses in the pipe but also for raising the culture by the height of the fall.

Although it generates less bubbles, this device with a centrifugal pump is also mechanically damageable for the microorganisms and for the gas lift. Indeed, in order to overcome the pressure losses, there is generation, at each passage at right angles to the pumping means, of mechanical forces which may impede the growth of the microorganisms and cause mortalities within the culture. The propipeion performances are then found to be altered, sometimes in a redhibitory way.

For example, it was seen that it is not possible to cultivate certain so-called fragile micro-algae in photobioreactors including centrifugal pumps for circulating the culture. These fragile micro-algae seem to be all the more sensitive to mechanical stresses since they form chains and/or they have appendices such as bristles, flagella, and spicules. Certain micro-algae, such as for example the algae of the *Haematococcus pluvialis* type, lose their flagella and encyst by forming a thick and resistant cell wall. On the other hand, other micro-algae such as for example the algae of the *Chlorella vulgaris* or *Nannochloropsis oculata* kind, do not have any appendage and have a thick cell wall, so that the latter resist to passing into the pumping means and notably into the centrifugal pumps.

However, it is difficult to identify the nature of the mechanical stresses having an influence on the survival and growth of the microorganisms. Most authors agree for stating that shearings and accelerations have the most influence. Shearings generate tensions which may alter the cell integrity with tearing of the wall of the microorganisms and effusion of the cytosol. Accelerations alter the structure of the cell by increasing the gravitational field.

Living cells are poorly prepared for these forces, and perhaps even more, aquatic cells which live in hydrostatic equilibrium and which have not developed any structure capable of overcoming a gravitational field. Furthermore, aquatic cells are sensitive to threshold values and also probably to the changes and to the duration of exposure. In the present state of knowledge, it is difficult to predict the mechanical effects of hydrodynamic conditions imposed to the cells.

One of the objects of the present invention is to reduce the mechanical effects imposed to the microorganisms, notably the effects of the shearing and acceleration type, in order to extend the number of cultivable species inside the reactor to those which are the most sensitive to these damageable mechanical effects, in other words provide a reactor allowing the cultivation of fragile microorganisms, such as for example the fragile micro-algae mentioned above.

Further, the applicant observed that the culture yield of photobioreactors equipped with a gas lift or a centrifugal pump was limited notably because of the formation of bubbles. Indeed, the applicant established that the culture yield partly depends on phenomena involved in the gas-liquid transfer in order to avoid losses and reduce this significant item of expenditure. Modeling the gas-liquid transfer of carbon dioxide intended for the reaction and of oxygen which it produces, requires determination of the transfer rate which depends on the surface transfer coefficient.

The surface transfer coefficient is a key parameter which expresses the performances of a gas/liquid exchange system in the stable condition. This surface transfer coefficient is equal to the propipe of the bulk transfer coefficient of material towards the liquid "KL" ($m \cdot s^{-1}$) and of the interface area reduced to the volume "a" ($m^{-1}$), wherein:

$$a = (\alpha_G \cdot S)/V$$

a: Interface area reduced to the volume ($m^{-1}$);
$\alpha_G$: Phase retention coefficient;
S: Contact surface area ($m^2$); and
V: Volume of the reactor ($m^3$).

The surface transfer coefficient therefore depends on the geometry of the gas/liquid exchange system but also on the physicochemical properties of the liquid and of the gas. In the case of a gas/liquid exchange within a vertical bubble column, the exchange surface area depends on the number of bubbles and on their size. The population of bubbles generated by gas injection in a liquid depends on the injection flow rate, on geometry of the injector, and on the pressure difference on either side of the latter.

The present invention notably has the goal of providing a photosynthetic reactor which allows bulk cultivation of photosynthetic microorganisms and its extension to the most fragile species, with a reactor which meets the following problems:

reduce or even avoid mechanical stresses generally related to stirring and to circulation of the culture medium and which reduce the survival and growth performances of photosynthetic microorganisms such as micro-algae and more particularly micro-algae in chains provided with appendages;

reduce or even avoid the propipeion of bubbles of small dimensions which may promote aggregation of organic molecules and the development of heterotrophic microorganisms for which they are used as a substrate;

while achieving photon transfer, in order to deliver the solar radiation to the photosynthetic microorganisms, the mass transfer or the gas/liquid transfer indispensable for providing the carbon and removing the oxygen, and the thermal transfer, in order to remove the calories brought by the radiation and maintain the culture at the right temperature; and while maintaining mechanical conditions preserving the integrity of the cells and avoiding the exchanges with the surrounding medium lending themselves to contaminations and disseminations.

SUMMARY

For this purpose, it proposes a suitable photosynthetic reactor for the cultivation of photosynthetic microorganisms, notably algae, comprising:

at least one photosynthetic reaction pipe in which the liquid culture medium circulates and which is provided with at least one substantially horizontal reaction section and made at least partly in a material transparent to light radiation, said pipe having a low end positioned in the low portion of the reactor and a high end positioned in the high portion of the reactor above the low end;

at least one return pipe ensuring the fluidic connection between the low end and the high end of the reaction pipe;

at least one means for circulating the liquid culture medium;

at least one gas injection means positioned in the reaction section or upstream from said reaction section with respect to the direction of circulation of the gas, said gas injection means allowing gas to be injected into the reactor; and at least one exhaust means positioned in the high portion of the reactor and allowing escape of the gas injected into the reactor;

in which the placement of the gas injection means and/or the conformation of the reaction pipe or of the return pipe are designed so that the gas injected by the injection means moves up to the exhaust means while circulating in the reaction pipe, in a direction of circulation from the low end up to the high end of the reaction pipe, so that the injected gas and the liquid culture medium establish a two-phase gas/liquid flow in the substantially horizontal reaction section.

With a reactor according to the invention, the liquid culture medium and the gas simultaneously circulate in contact with each other along the substantially horizontal and transparent reaction section and exchange some components along their common path. The gas injected at the low point escapes at the high point of the reactor while the liquid circulates according to a loop under the impetus of one or more circulation means. The exchanges are proportional to the length of the transparent section(s), so that the effect of the latter is reduced with which it is possible to contemplate large increases in scale.

The reactor according to the invention is thus specially designed in order to increase the efficiency of the gas-liquid transfer and for reducing the mechanical stresses imposed to the organisms in the culture in order to extend propipeion to fragile species. Further, with the reactor according to the invention it is possible to limit the formation of bubbles of small diameter and thereby reducing the development of oxygen-consuming heterotrophic microorganisms. Indeed, with the reactor according to the invention, the gas-liquid transfer no longer occurs inside a vertical bubble column but along a substantially horizontal pipe section in which the flow is subject to conditions of the horizontal two-phase type.

Thus, the reactor according to the invention gives the possibility of obtaining gas-liquid exchanges through an interface formed at the free surface of the liquid in the reaction pipe and more particularly in the substantially horizontal reaction sections in which the circulation of the gas and of the liquid is substantially established horizontally according to gas/liquid two-phase flow conditions of the laminated or slug or elongated bubble flow.

Unlike the principle mentioned above according to which the reaction only occurs in the liquid phase, the applicant started from the principle according to which the gas is an integral part of the reaction and should be admitted into the reaction space in the same way as the liquid. By preferring horizontal two-phase flow conditions (laminated, slug or elongated bubble flow), the exchange surface area between the gas and the liquid is extended to the whole of the path in the reaction pipe (in other words along each substantially horizontal reaction section) with significantly less abundant propipeion of bubbles than in the case of the reactors of the prior art, therefore reducing the deleterious effect observed for these bubbles.

Further, in the reactor according to the invention, the setting of the liquid culture medium into circulation is ensured by one or more circulation means generating reduced shearing and centrifugal forces: the circulation function being disassociated from that of gas-liquid exchange unlike the case of reactors with a gas lift.

According to one characteristic, the reactor comprises at least one liquid injecting means for allowing injection of the liquid into the reactor, the exhaust means being conformed so as to allow escape of the excess volume of liquid in the reactor at the same time as escape of the injected gas. With this, it is thereby possible to renew the liquid medium and ensure escape of excess liquid volume, in addition to the injected gas volume.

In a first embodiment, the circulation means is positioned in the return pipe so as to circulate the liquid culture medium in the reaction pipe from the low end up to the high end of said reaction pipe, in the same direction of circulation as the injected gas. In this embodiment, the gas and the liquid circulate in the same direction inside the reaction pipe and one refers to a co-current circulation mode. With this co-current mode, the fluids (gas and liquid) move in the same direction and their contact lasts for a few seconds before being separated because of the differences in velocity. The co-current circulation of the gas and of the liquid generates an exchange surface area proportional to the length of the reaction pipe, which allows increases in the size of the latter without having to multiply the number of degassing and carbonation apparatuses.

In a second embodiment, the circulation means is placed in the return pipe in order to set the liquid culture medium in circulation in the reaction pipe from the high end as far as the low end of said reaction pipe, in a direction of circulation opposite to the circulation direction of the injected gas. In this embodiment, the gas and the liquid circulate in opposite directions inside the reaction pipe and one refers to a counter-current circulation mode. The applicant thus observed that counter-current circulation is more performing than co-current circulation although resorting to the counter-current mode poses regulation problems since, with the counter-current mode, the fluids separate immediately so that they are found in contact again only much later.

According to one characteristic, the gas injection means is positioned in the low portion of the reactor, between the circulation means and the low end of the reaction pipe. In this configuration, the circulation means tends to discharge the gas towards the reaction pipe, thereby avoiding accumulation of gas in the return pipe.

According to another characteristic, the return pipe has a difference in height located between the circulation means and the gas injection means, said height difference forming a difference of levels between the circulation means and the gas injection means in order to avoid that the gas injected by the injection means moves in direction of the circulation means.

In a particular embodiment, the circulation means is a mechanical propulsion means positioned in the return pipe.

Preferentially, the circulation means comprises a propeller driven into rotation by a motor, and the return pipe has a housing with a widened cross-section inside which said propeller is mobile in rotation.

Advantageously, the housing of the propeller is positioned between a divergence area and a convergence area of the circulation of the liquid culture medium, in order to ensure in the return pipe, hydraulic continuity without any sudden change in the velocities with the purpose of limiting the pressure losses, the accelerations and shearing forces experienced by the microorganisms.

According to an advantageous feature, the return pipe has in the high portion a widened area, and the exhaust means is positioned in said widened area of the return pipe, thereby allowing a decrease in the velocity of the liquid in the widened area where escape of the gas occurs and thereby preventing gas from being driven downwards by the liquid.

According to another feature, the exhaust means is positioned upstream from the means for circulating the liquid culture medium with respect to the direction of circulation of the gas, in order to prevent the gas from circulating through said circulation means and becoming detrimental to its operation.

In a preferred embodiment, the reactor comprises at least one cleaning body conformed for circulating inside the reaction and return pipes and for passing through the means for circulating the liquid culture medium. The cleaning body(ies) thereby allow cleaning of the inside of the reactor.

Advantageously, the cleaning body is conformed so as to let through at least partly the gas circulating inside the reaction pipe while being adapted so as to be driven by the circulation of the liquid culture medium, so that the body does not have any influence on the difference in velocities between the gas and the liquid medium; said difference in velocities directly having an influence on the mass transfers between the liquid phase and the gas phase.

Still advantageously, the cleaning body is made in the form of a brush comprising an assembly of bristles, hairs, strands or equivalent or in the form of hollow sphere in an elastomeric material, at least one portion of the surface of which is pierced with holes. Thus, the emerging bristles or the holes let through the gas while the immersed portion of the cleaning body forms an obstacle to the circulation of the liquid medium so as to be able to be carried away with this liquid medium.

In a particular embodiment, the reactor comprises:

a short-circuit pipe positioned in parallel on the return pipe and connecting two connection points provided on the reactor, including one first connection point positioned on the reaction pipe and a second connection point positioned on the return pipe or on the reaction pipe;

two valves positioned on either side of said first connection point with one of the valves positioned on the short-circuit pipe;

two valves positioned on either side of said second connection point with one of the valves positioned on the short-circuit pipe;

so that the handling of the valves gives the possibility of isolating the portion of the reactor located between the first and the second connection points on the side of the reaction pipe and the gas/liquid culture medium mixture circulates in the short-circuit pipe and in the non-isolated portion of the reactor located between the first and second connection points on the side of the return pipe.

In this embodiment, the reactor is provided with a short-circuit pipe which allows isolation of a subvolume of the reaction pipe. It is thereby possible, in a first phase that the subvolume be isolated, inoculated and cultivated. Next, when the concentration attains a sufficient level in this subvolume, the four valves are switched into the opposite state so that the remainder of the reactor is put into circulation and inoculated by the subvolume.

The invention also relates to an assembly of photosynthetic reactors suitable for the cultivation of photosynthetic microorganisms comprising at least two reactors according to the invention, i.e. a first and second reactor, and comprising at least one connection pipe ensuring a fluidic connection between the first reactor and the second reactor and at least one valve positioned on said connection pipe.

This assembly is particularly advantageous in order to have two or more reactors in parallel which are connectable, notably for allowing inoculation via the connection pipe, in order to achieve a propipeion assembly which is propipeive and consistent. In order to make inoculation of one reactor possible by its neighbor, the concentration of which will have attained an advanced stage, it is possible to interconnect both reactors so that their contents are mixed together.

According to one feature, the assembly comprises two connection pipes between both reactors, each provided with a valve, including:

a first connecting pipe connecting an inlet point positioned on the first reactor upstream from the means for setting circulation in said first reactor to an outlet point positioned on the second reactor downstream from the means for setting circulation in said second reactor:

a second connection pipe connecting an inlet point positioned on the second reactor upstream from the circulation means for said second reactor to an outlet point positioned on the first reactor downstream from the circulation means for said first reactor.

In order to proceed with the inoculation of the second reactor from the first reactor already operating and the concentration of which has attained the operating level, the second reactor to be inoculated is filled with a sterile nutritive medium and circulation is established by opening both valves of the connection pipes in order to establish a cross-exchange between both reactors. The interconnection between both reactors is established between the upstream portion and downstream portion of the circulation means so that the obtained propelling force with the circulation means promotes exchange circulation.

According to another feature, the assembly comprises a pump interposed on either one of the connection pipes in order to reduce the duration of exchanges between both reactors.

The invention also relates to a method for cultivating photosynthetic microorganisms, notably algae, using a reactor according to the invention and comprising the following steps:

injecting a liquid culture medium into the reactor according to a controlled flow rate;

injecting a gas into the reactor according to a controlled flow rate with the gas injection means;

putting the liquid culture medium into circulation with the circulation means;

controlling the circulation means and the gas injection means so as to establish in the reaction section, gas/liquid two-phase flow conditions of the laminated or slug or elongated bubble flow type.

As described above, the establishment of substantially horizontal gas/liquid two-phase flow conditions of the laminated or slug or elongated bubble flow type has many advantages such as repipeion in the propipeion of bubbles and increase in the yield of the reactor by notably increasing the exchange surface area between the gas and the liquid.

According to a feature, the control step comprises a step for controlling the circulation rate of the liquid in the reaction pipe between about 0.1 and 0.2 m/s in order to establish two-phase flow conditions of the laminated flow type.

According to another feature, the control step comprises a step for controlling the circulation rate of the liquid in the reaction pipe between about 0.2 and 1 m/s in order to establish two-phase flow conditions of the slug or elongated bubble flow type.

Advantageously, the control step comprises a step for controlling the gas circulation rate between about 0.5 and 0.8 m/s corresponding to velocity conditions suitable for the flow rates required for the reaction.

Still advantageously, the circulation means comprises a propeller driven into rotation by a motor and in which the speed of rotation of the propeller is less than about 100 revolutions per minute, so as to limit mechanical stresses within the liquid culture medium.

BRIEF DESCRIPTION OF THE DRAWINGS

Other features and advantages of the present invention will become apparent upon reading the detailed description thereafter of an exemplary non-limiting embodiment, made with reference to the appended figures wherein.

DETAILED DESCRIPTION

Figure 1:
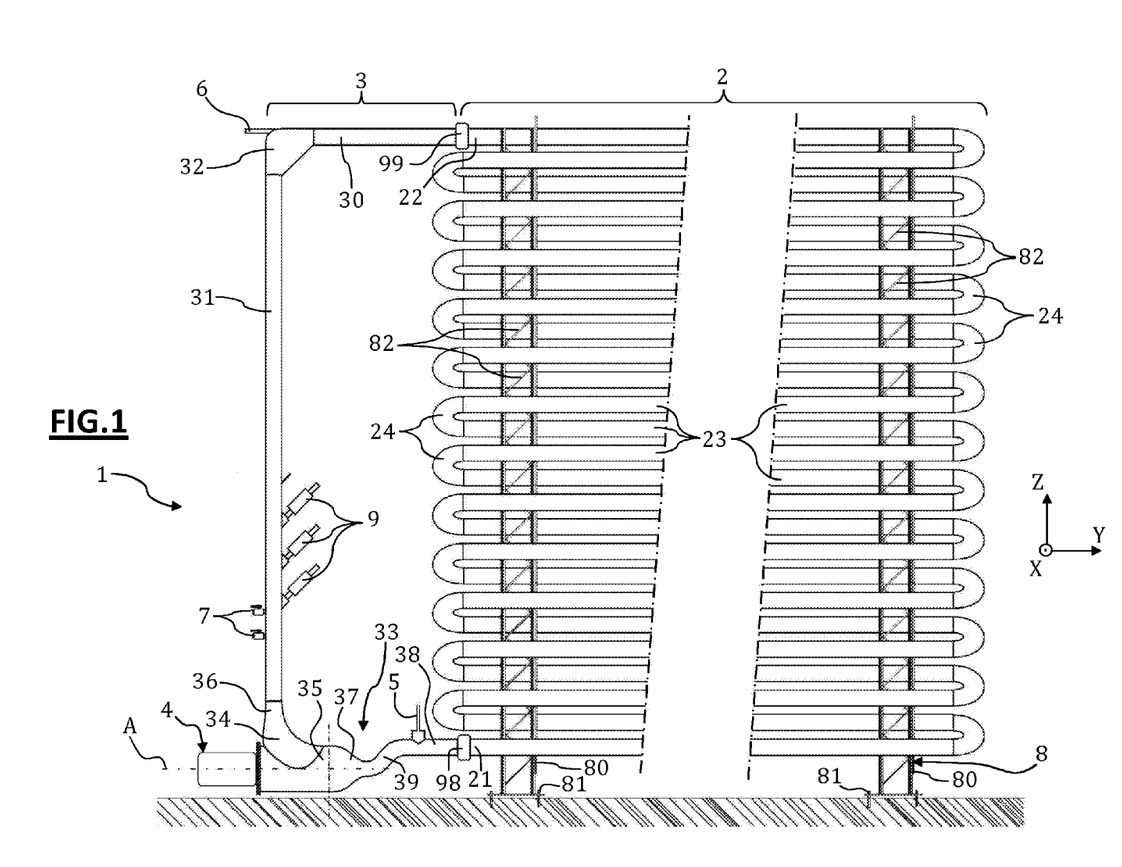
FIG. 1 is a schematic front view of a photosynthetic reactor according to the invention.
Figure 2:
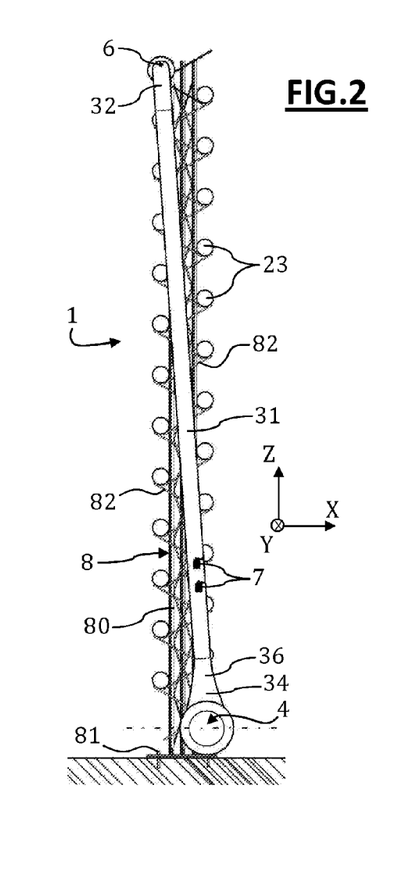
FIG. 2 is a schematic side view of the reactor illustrated in FIG. 1.
Figure 3:
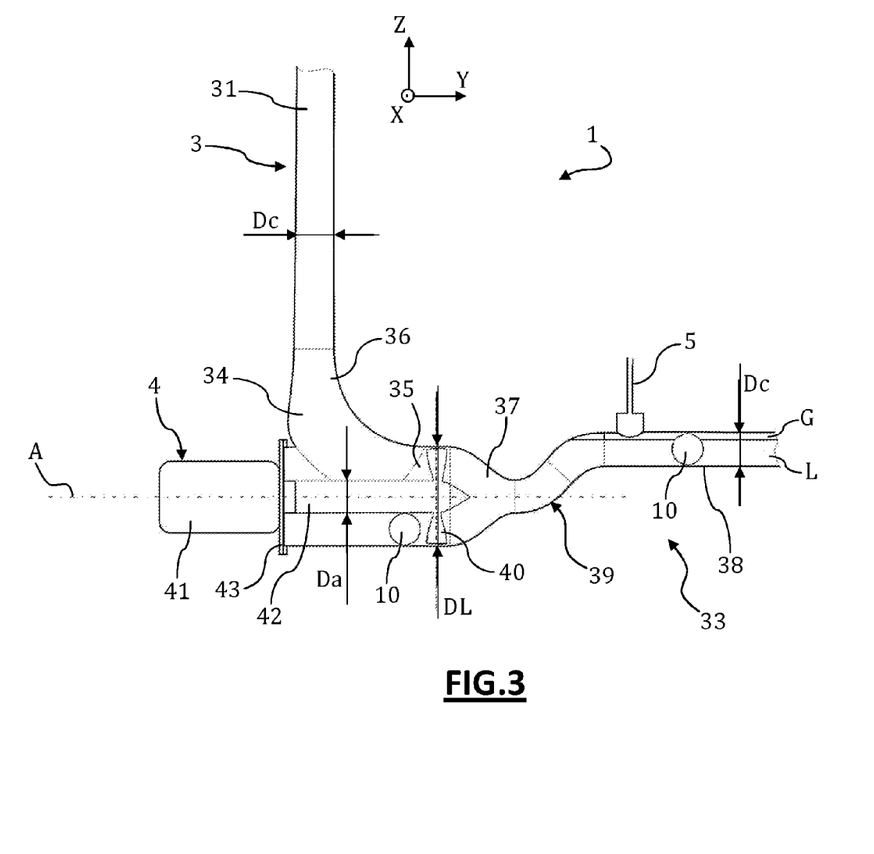
FIG. 3 is a partial schematic view of the inside of the reactor illustrated in FIG. 1.

FIGS. 1 to 3 illustrate a photosynthetic reactor 1 according to the invention and which is suitable for the cultivation of photosynthetic microorganisms, notably algae, and in particular for the cultivation of photosynthetic microorganisms which are fragile with respect to mechanical stresses and therefore unsuitable for cultivation in reactors of the state of the art.

The reactor 1 includes:

at least one photosynthetic reaction pipe 2 in which the liquid culture medium circulates, said reaction pipe 2 having a low end 21 positioned in the lower portion of the reactor 1 and a high end 22 positioned in the high portion of the reactor 1 above the low end 21;

at least one return pipe 3 ensuring the fluidic connection between the low end 21 and the high end 22 of the reaction pipe 2;

at least one means 4 for circulating the liquid culture medium;

at least one gas injecting means 5 allowing injection of the gas into the reactor; and at least one exhaust means 6 positioned in the high portion of the reactor 1 and allowing escape of gas injected into the reactor 1;

at least one liquid injecting means 7 allowing injection of liquid into the reactor 1.

It is quite understood in the sense of the present application that the use of the terms <<low>> and <<high>> for designating the portions of the reactor 1 as well as the use of a term such as <<above>>, refer to the relative placement of the elements or portions of the reactor along the vertical direction illustrated by the arrow Z in the figures.

As visible in FIG. 1, the reaction pipe 2 comprises several horizontal sections 23, said reaction sections, successively connected through bent sections 24, the horizontal sections 23 and the bent sections 24 are connected in series at intervals so that the reaction pipe 2 has the shape of a continuous conduit as an accordion or a spiral between its low end 21 and its high end 22. This reaction pipe 2 mainly extends along a vertical plane with the horizontal sections 23 successively placed above each other.

As visible in FIG. 2, the horizontal sections 23 are successively positioned on either side of a vertical supporting structure 8 comprising:

vertical pillars 80 fixed in the ground via screws 81; and crossbars 82 firmly attached to the vertical pillars 81 and supporting the horizontal sections 23.

The supporting structure 8 spreads the weight of the reaction pipe 2 with both of its vertical pillars 81 which are spaced out from each other by a distance which does not exceed the span limit of the horizontal sections 23 causing rupture of said horizontal sections 23 filled with liquid and gas because of their weight, and crossbars 82 which maintain the horizontal sections 23 at equal vertical and horizontal distances from each other.

The horizontal sections 23 are at least partly made in a material transparent to solar radiation, such as for example in a glass material or a synthetic material of the plastic or acrylic polymer type such as PLEXIGLAS™ These horizontal sections 23 are made in the form of rectilinear pipes with a circular cross-section of diameter Dc. The bent sections 24 are made in the form of 180° bent pipes for connecting end to end successive horizontal sections 23. The bent sections 24 are of circular section of diameter Dc just like the horizontal sections.

The return pipe 3 has the general shape of a "C" and successively includes:

a horizontal upper section 30 connected to the high end 22 of the reaction pipe 2 via a connector 99.

a vertical or slightly oblique central section 31, as visible in FIG. 2, connected to the upper section 30, through a first bend 32 forming an angle of about 90°; and a lower section 33 connected to the central section 31 through a second bend 34 forming an angle of about 90° on the one hand and to the low end 21 of the reaction pipe 2 via a connector 98 on the other hand and coming into the extension of the lowest horizontal section 23 of the reaction pipe 2, said to be the first horizontal section.

The return pipe 3 is made in a material which is not transparent to solar radiation and/or which may be positioned inside closed premises away from light, while the reaction pipe 2 is exposed to solar light, optionally under a greenhouse.

The upper section 30 is made as a rectilinear pipe with a circular section of diameter Dc equal to that of the horizontal sections 23 of the reaction pipe 2. The upper section 30 comes into the extension of the horizontal section 23 located the highest of the reaction pipe 2, said to be the last horizontal section, and extends at the same vertical level than the latter horizontal section 23.

The central section 31 is also made as a rectilinear pipe of circular cross-section of diameter Dc equal to that of the horizontal sections 23 of the reaction pipe 2. This central section 31 extends along a vertical or slightly oblique direction with respect to the vertical direction Z.

The first bend 32, positioned in the high portion, has a widened cross-section with respect to the upper section 30 and to the central section 31 of the same diameter Dc. The exhaust means 6 is positioned on said first bend 32 and appears as a pipe with predetermined dimensions which opens out inside the first bend 32. Thus, the passage cross-section at the first bend 32 is increased in order to reduce the flow rate of the liquid in said first bend 32 and avoid gas from being carried away downwards into the central section 31. The exhaust means 6 is positioned in the high portion with respect to the highest horizontal section 23 of the reaction pipe 2, so that only the excess liquid escapes from the reactor 1 at the same time as the gas. The exhaust means 6 is calibrated so as to allow the excess liquid volume in the reactor 1 to escape at the same time as the injected gas escapes.

The reactor 1 comprises two liquid injection means 7 positioned on the central section 31, i.e. a first and second injection means allowing the liquid culture medium and the inoculum to be respectively injected into the reactor 1. These injection means 7 appear in the form of injection ports allowing connection to a source with control of asepsis.

The reactor 1 further comprises one or more sensors 9 positioned on the return pipe 3 and more particularly on the central section 31, and adapted for providing the signals required for controlling the reaction, notably signals representative of temperature, pH, dissolved oxygen level and turbidity of the liquid medium. This control is notably used for regulating the gas and liquid injections into the reactor 1.

The lower section 33 has a housing 35, with a widened cross-section with respect to the diameter Dc of the central section 31, intended to partly receive the circulation means 4. This housing 35 is located in the direct extension of the second bend 34 and extends along a horizontal main direction A.

The circulation means 4 illustrated in FIGS. 1 to 3 is positioned in the return pipe 3, at least partly inside the housing 35, in order to set the liquid culture medium in circulation in the reaction pipe 2 from the low end 21 to as far as the high end 22 of said reaction pipe 2, in other words from bottom to top inside the reaction pipe 2. In this configuration, the liquid medium circulates from the upper section 30 towards the lower section 33 inside the return pipe 3, in other words from top to bottom inside the return pipe 3 and its central section 31.

The circulation means 4 is made as a mechanical propulsion means which comprises a propeller 40 driven into rotation by a rotary motor 41 via an output shaft 42 of said motor 41. The motor 41 is positioned outside the reactor 1, at the second bend 34, and is attached on a plate 43 removably attached on the walls of the return pipe 3, notably by means of fixing screws. The output shaft 42 sealably crosses said plate 43, opens into the inside of the housing 35 and supports the propeller 40 which is thus mobile in rotation inside this housing 35. The output shaft 42 and the propeller 40 rotate around a horizontal axis of rotation A and the propeller 40 extends in a substantially vertical plane.

The location of the circulation means 4 in the lower portion of the return pipe 3 provides easy access for maintenance. In the example illustrated in FIGS. 1 to 3, it is actually easy to maintain the propeller 40 by disassembling the plate 43 closing the housing 35 for receiving the propeller 40. The mechanical assembly formed by the motor 41, the plate 43, the output shaft 42 and the propeller 40 may be simply freed by horizontal translation, for example by bearing upon the ground.

The lower section 33 has a horizontal rectilinear portion 38 made in the form of a rectilinear pipe with a circular cross-section of diameter Dc equal to that of the horizontal sections 23 of the reaction pipe 2. The rectilinear portion 38 is positioned between the housing 35 and the low end 21 of the reaction pipe 2. The rectilinear portion 38 comes into the extension of the first horizontal section 23 (the lowermost located one of the reaction pipe 2), and extends at the same vertical level as this first horizontal section 23.

Hydraulic continuity without any sudden change in the velocities is sought in the return pipe 3 in order to limit pressure losses, accelerations and shearing forces experienced by the photosynthetic microorganisms. The average velocity of the liquid medium decreases between the central section 31 and the lower section 33 because of the increase in the passage cross-section between the central section 31 and the housing 35, and then increases because of the inverse decrease in the passage cross-section between the housing 35 and the rectilinear portion 38. In order to ensure hydraulic continuity between the central section 31 and the rectilinear portion 38 of the lower section 33, a divergent tube 36 is positioned in the high portion of the second bend 34, in other words upstream from the housing 35 and from the propeller 40, and a convergent tube 37 is positioned between the housing 35 and the rectilinear portion 38, in other words downstream from the housing 35 and from the propeller 40.

The lower section 33 has a difference in height 39 located between the housing 35 and the rectilinear portion 38, and more particularly between the convergent tube 37 and the rectilinear portion 38. This difference in the height 39 is achieved in the form of two bends forming a difference of levels between the housing 35 and the rectilinear portion 38.

The gas injection means 5 is positioned on the rectilinear portion 38 of the lower section 33 of the return pipe 3, so that the gas G injected by the gas injection means 5 moves up as far as the exhaust means 6, while circulating in the reaction pipe 2, in a direction of circulation from the low end 21 to as far as the high end 22 of the reaction pipe 2, in other words from bottom to top inside the reaction pipe 2. In this configuration, the gas G and the liquid medium L circulate as a co-current, i.e. in the same direction of circulation, inside the reaction pipe 2.

The difference in height 39 is positioned upstream from the gas injection means 5 in order to avoid that the gas injected by the gas injection means 5 moves in the wrong direction, i.e. towards the housing 35 and the propeller 40, in particular when the motor 41 is at a standstill.

The location of the circulation means 4, and of the propeller 40 in particular, in the low portion of the central section 31 of the return pipe 3 and upstream from the gas injection means 5 is advantageous in order to allow discharge by having the injected gas be carried away horizontally in the rectilinear portion 38 of the lower section 33 of the return pipe 3.

The placement of the exhaust means 6 upstream from the circulation means 4 combined with the placement of the circulation means 4 upstream from the gas injection means 5 is advantageous in order to avoid circulation of the gas through the propeller 40 and interference with its operation. Indeed, the presence of gas hinders the operation of most of the mechanical propulsion means and in particular the propellers, and its accumulation should therefore be avoided, with the risk of having the propeller 40 cavitate.

As visible in FIG. 3, the gas G injected by the gas injection means 5 and the liquid culture medium L set into circulation by means of the propeller 40 establish together gas/liquid two-phase flow in the rectilinear portion 38 and therefore necessarily in the lowest horizontal section 23 of the reaction pipe 2. The gas G, as visible in FIG. 3, forms a blanket inside the rectilinear portion 38 and therefore the lowest horizontal section 23 of the reaction pipe 2; this blanket also forming in the following horizontal sections 23 as the gas gradually advances into the reaction pipe 2 to as far as the exhaust means 6.

Notably depending on the respective circulation rates of the gas and of the liquid medium, the gas/liquid two-phase flow will follow two-phase flow conditions of the laminated flow type (a continuous gas blanket) or of the slug or elongated bubble flow type (discontinuous gas blanket). These conditions of flow are possible since the gas circulation, either as a co-current or counter-current of the circulation of the liquid medium, is mainly accomplished in the horizontal rectilinear portion 38 of the lower section 33, in horizontal sections 23 and in the horizontal upper section 30. Of course, the gas rises in the reaction pipe 2 via the bent sections 24, but these gas upflows in the bent sections 24 are not detrimental to the laminated, slug or elongated bubble flow conditions observed in the horizontal sections 23.

Generally, the gas injection means 5 is positioned upstream from the first horizontal section 23 (the lowermost one in the reaction pipe 2) or optionally in said first horizontal section 23 with respect to the low-to-high flow direction of the gas inside the reaction pipe 2. It is also conceivable to provide several gas injection means in different points of the reaction pipe 2, over one or several horizontal sections 23, and optionally other gas exhaust means.

Figure 8A:
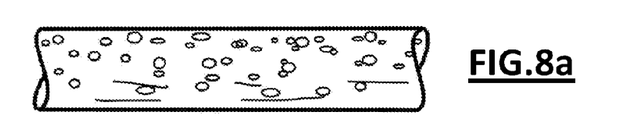
FIGS. 8a to 8f schematically illustrate several flow conditions in a horizontal conduit, respectively a flow with dispersed bubbles, a flow with elongated bubbles, a smooth laminated flow, a rippled laminated flow, a slug flow and an annular flow.
Figure 8B:
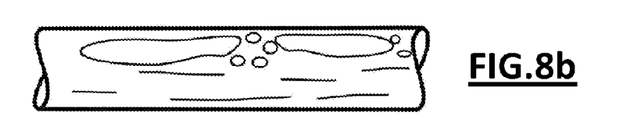
Figure 8C:
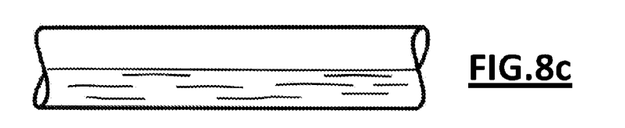
Figure 8D:
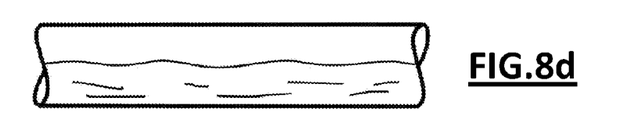
Figure 8E:
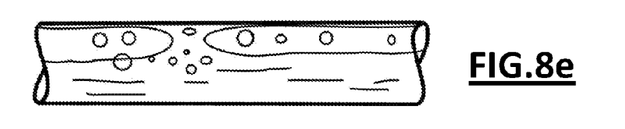
Figure 8F:
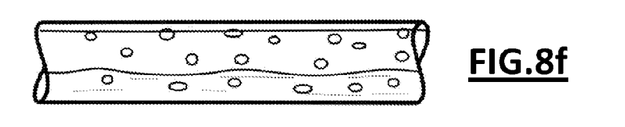

As regards the two-phase flows in horizontal conduits, investigations have shown several flow conditions depending on the conditions of velocity, diameter, temperature, on the nature, on the pressure of the circulating fluids, i.e. notably:

a flow with dispersed bubbles of the Mandhane AD typology, which is illustrated in FIG. 8a; and a flow with elongated bubbles of the Mandhane I typology which is illustrated in FIG. 8b;

laminated flow, or stratified flow, which is illustrated in FIG. 8c with rippled stratified flow and in FIG. 8d with smooth stratified flow of the Mandhane SS and SW typology respectively;

slug flow of the Mandhane I typology which is illustrated in FIG. 8e;

annular mist flow of the Mandhane AD typology which is illustrated in FIG. 8f.

In the case of the present invention, the preferential flow conditions are located at the SS/I transition in the Mandhane typology, i.e. between the stratified conditions and the slug flow or elongated bubble conditions. Under the stratified conditions, the gas/liquid interface is formed by the free surface, the width of which varies with the level of the liquid in the pipes. Under the slug or elongated bubble conditions, the gas/liquid interface is formed by the floor and the ceiling of the slug or of the elongated bubble.

In the case of the present invention, with a diameter Dc for the horizontal sections 23 of the order of a few centimeters, for example comprised between about 4 and about 15 centimeters, the gas/liquid two-phase flow in the horizontal sections 23 will follow stratified flow conditions for velocities of the liquid comprised between 0.1 and 0.2 m/s, and slug or elongated bubble flow conditions for velocities of the liquid comprised between 0.2 and 1 m/s.

Liquid rates of more than 0.2 m/s may be selected in order to promote mixing in the liquid culture medium, thereby implying that the two-phase flow in the horizontal sections 23 will follow slug flow or elongated bubble flow conditions.

The gas/liquid exchanges or transfers substantially vary in proportion with the velocity difference between the circulation of the gas and the circulation of the liquid medium, it is particularly advantageous to maintain a high velocity difference between the gas circulation and the liquid circulation. The applicant has thereby observed that the velocity of the gas should be stabilized between 0.5 and 0.8 m/s for the gas flow rates required for the photosynthetic reaction, and that the velocity difference required for the exchanges is easy to obtain with co-current circulation.

Co-current circulation of the gas and of the liquid generates an exchange surface area proportional to the length of the reaction pipe 2, which makes increases of the length of said reaction pipe 2 possible without having to multiply the number of de-gassing and carbonatation apparatuses. Although this intropipeion of gas into the reaction pipe involves a repipeion in the liquid reaction volume, ranging up to 15% depending on the gas flow rate, inside the reaction pipe 2, this repipeion in the liquid reaction volume is for a large part compensated by the increase in the volume propipeivity which results from the decrease in the length of the optical path. From the point of view of microbiological quality, the absence of small bubbles in the reactor 1 according to the invention is of great interest, as described above and this reactor 1 also is of interest in terms of cost since it does not require any de-gassing and carbonatation apparatus.

The applicant also observed that it is possible to increase the velocity difference between the gas circulation and the liquid circulation, and therefore to increase the gas/liquid transfers, by applying a counter-current circulation within the reaction pipe 2, in other words by ensuring that the liquid medium circulates from top to bottom inside the reaction pipe 2. Thus, in a non-illustrated embodiment, the circulation means 4 is positioned in the return pipe 3 in order to have the liquid culture medium circulate in the reaction pipe 2 from the high end 22 to as far as the low end 21 of said reaction pipe 2, in a direction of circulation opposite to the direction of circulation of the injected gas, in other words from top to bottom inside the reaction pipe 2. In this alternative, the liquid medium circulates from the lower section 33 towards the upper section 30 inside the return pipe 3, in other words said to be from bottom to top inside the return pipe 3 and its central section 31. In order to achieve such counter-current circulation, the circulation means 4 may be turned upside down by 180° in order to operate in the other direction of circulation in the same location as in the previous case, said to be co-current, since it has the advantage of being without any gas circulation, partly inside the same adequate housing 35. The gas injection 5 and exhaust 6 means may advantageously be maintained at the same locations than in the previous case, since they maximize the length of the common path and therefore the duration of the fluidic contact.

The following table compares the performances of three photosynthetic reactors implanted under the 42$^{nd}$ parallel of latitude and consisting in a transparent reaction pipe of length 215 m and with an inner diameter of 76 mm, with an overall capacity of 1,000 liters.

|  | «Bubble column» reactor | «Co-current» reactor according to the invention | «Counter-current» reactor according to the invention |
| --- | --- | --- | --- |
| S = Contact surface area (m$^2$) | 2 | 7 | 7 |
| KL · a = Surface transfer coefficient (hour$^{-1}$) | 1 | 3 | 4 |
| VM = Maximum oxygenation rate of the liquid medium (mg/L/hour) | 44 | 44 | 44 |
| VE = O$_2$ extraction rate (mg/L/h) | 11 | 47 | 58 |
| Efficiency = VE/VM (percentage) | 25 | 107 | 132 |

The <<bubble column>> reactor corresponds to the reactor of the state of the art described above and including a gas lift. This <<bubble column>> reactor comprises a bubble column with a height equal to 4 m and with a diameter equal to 76 mm identical to that of the reaction pipe.

The <<co-current>> reactor according to the invention corresponds to the reactor according to the invention in which a co-current circulation mode is established in the reaction pipe, while the <<counter-current>> reactor according to the invention corresponds to the reactor according to the invention in which a counter-current circulation is established in the reaction pipe.

The maximum oxygenation rate VM was calculated for a species of algae with rapid growth during the peak photosynthetic activity, i.e. during the summer period and at noon.

The applicant thus confirms that oxygen extraction by the known reactor with a <<bubble column>> is insufficient and limits the efficiency of the reactor, while the <<co-current>> and <<counter-current>> reactors according to the invention efficiently cover the oxygen extraction needs.

The gas/liquid transfer and therefore the oxygen extraction are more efficient with the reactors according to the invention where the gas/liquid interface is accomplished on the whole of the path of the reaction pipe, than with the known <<bubble column>> reactor, where the gas/liquid interface is limited to the small bubbles and where the oxygen extraction is localized. This confirms the opinion of the applicant, mentioned above, according to which the gas is an integral part of the reaction and should be admitted into the reaction volume on the same basis as the liquid.

Figure 6A:
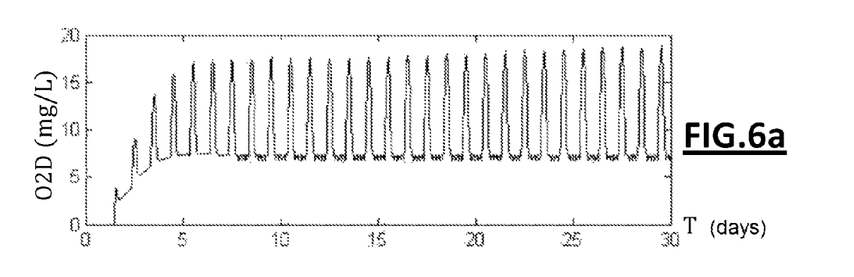
FIGS. 6a and 6b respectively illustrate the change in dissolved oxygen and in dissolved carbon dioxide over time for a first reactor according to the invention.
Figure 6B:
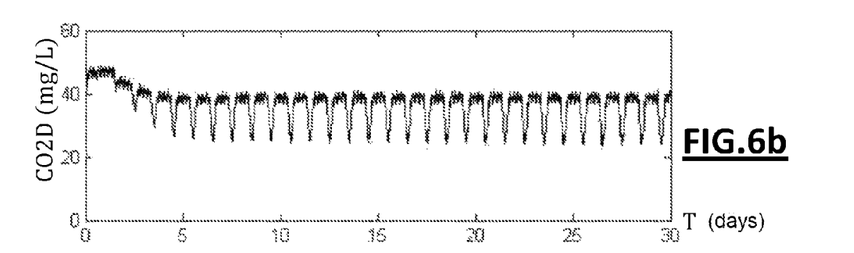
Figure 7A:
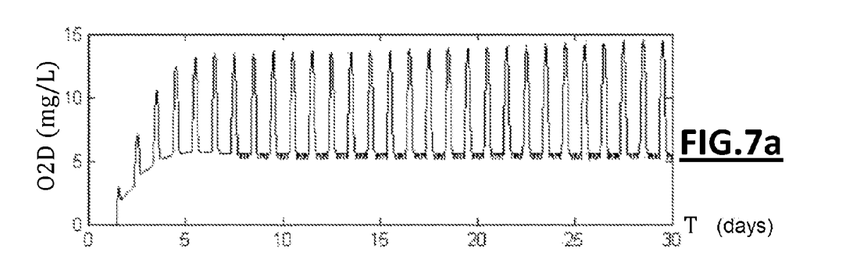
FIGS. 7a and 7b respectively illustrate the change in dissolved oxygen and in dissolved carbon dioxide over time for a second reactor according to the invention.
Figure 7B:
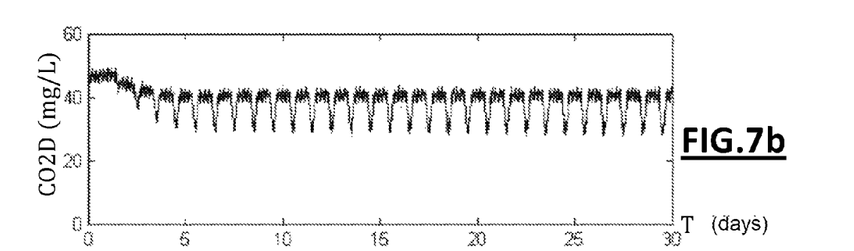

Further, the counter-current circulation mode is more performing than the co-current circulation mode. FIGS. 6 and 7 confirm this point by illustrating numerical stimulations of gas exchanges in the case of a culture of micro-algae of the *Porphyridium cruentum* kind in a reactor receiving a gas flow containing 3% of CO$_2$, and 0% of O$_2$ injected in an amount of 6 liters per minute with a co-current circulation mode (FIGS. 6*a* and 6*b*) and a counter-current circulation mode (FIGS. 7*a* and 7*b*), wherein:

FIG. 6*a* illustrates the change in the dissolved oxygen O2D (mg/L) over time (days) for a co-current reactor;

FIG. 6*b* illustrates the change in the dissolved carbon dioxide CO2D (mg/L) over time (days) for a co-current reactor;

FIG. 7*a* illustrates the change in the dissolved oxygen O2D (mg/L) over time (days) for a counter-current reactor; and FIG. 7*b* illustrates the change in the dissolved carbon dioxide CO2D (mg/L) over time (days) for a counter-current reactor.

These numerical simulations therefore confirm the superior efficiency of the counter-current mode. The co-current circulation mode however remains sufficient the whole time in order to maintain the oxygen content below 20 mg/L, in other words the co-current mode is sufficient if the toxicity threshold is located at 20 mg/L.

However, resorting to the counter-current mode poses regulation problems. Indeed, with the co-current mode, the fluids (gas and liquid) circulate in the same direction and their contact is achieved during a few seconds before being separated from each other because of the velocity differences. On the other hand, with the counter-current mode, the fluids separate immediately so as to be again in contact only much later.

Generally, it is possible to act on the gas flow rate and on the circulation rate of the liquid culture medium, as well as on the light intensity variations in order to adapt them to the different cultivated species: for example a strong gas flow rate is desirable with strong light intensity and when the algal species exhibits rapid growth in order to increase the gas-liquid exchanges. However, one has to take into account the fact that a variation of the gas flow rate causes that of the culture volume. Thus, increasing the gas flow rate causes a decrease in the liquid volume which may lead to de-flooding of the last horizontal section 23 (the uppermost located one) and to interruption of the circulation in the circulation pipe 2.

As visible in FIG. 3, the reactor 1 may also comprise one or more cleaning bodies 10 conformed for circulating inside the reaction 2 and return 3 pipes in order to clean the inside of these pipes 2 and 3. In order to be able to circulate in a loop in the reactor 1, the cleaning body(ies) 10 is(are) also conformed so as to pass through means 4 for circulating the liquid culture medium, in other words through the blades of the propeller 40 in the particular embodiment described above.

The cleaning bodies 10, preferably spherical, have a diameter substantially equal to the inner diameter Dc of the reaction pipe 2 and of its horizontal 23 and bent 24 sections; the cleaning of the reactor 1 essentially concerning the inner wall of the reaction pipe 2 where cultivation of the micro-organisms takes place. The cleaning bodies 10 are preferably in flexible material in order to absorb by deformation the mechanical stresses of the circulation means 4, for example the impacts of the blades of the propeller 40 during the crossing of the housing 35.

The housing 35 is advantageously of circular section, at least in the plane of rotation of the propeller 40, i.e. the vertical plane at right angles to said propeller 40. As visible in FIG. 3, this circular cross-section of the housing 35 is of a diameter DL slightly larger than the diameter of the propeller 40. This diameter DL is also larger than the diameter Dc of the reaction pipe 2 and of the central section 31 of the return pipe 3 so that the propeller 40 may let through the cleaning bodies 10. As indicated above, this increase in the diameter is expressed by a repipeion in the linear velocities of the fluid and in the speeds of rotation of the propeller. In this case, the diameter DL of the housing 35 decreased by the diameter Da of the output shaft 42 of the motor 41 should be at least double the diameter Dc of the reaction pipe 2 so that the cleaning bodies 10 may freely circulate, carried off by the liquid reaction medium, including through the propeller 40, i.e.:

$$DL-Da=2 \cdot Dc.$$

In the embodiment illustrated in FIG. 3, the diameter DL is equal to triple the inner diameter Dc of the reaction pipe 2 and the diameter Da of the output shaft 42 is equal to the inner diameter Dc of the reaction pipe 2. In this configuration, the cleaning bodies 10 of diameter Dc may circulate in the annular portion with a width equal to Dc, extending between the inner wall of the housing 35 and the shaft 42, and may thereby pass more easily between the blades of the propeller 40.

In order to reduce the obstacle formed by the blades of the propeller 40 for these cleaning bodies 10 and for the micro-organisms, these blades are preferably limited to one in number (thereby forming a sort of Archimedes' screw) or to two. In order to decrease the sweeping surface area of the blades and the mechanical effects resulting from this, the speed of rotation of the propeller 40 will be low and preferably less than 100 revolutions per minute.

The circulation of the cleaning bodies 10 in the horizontal sections 23 may have the effect by making the gas and liquid medium circulation rates substantially identical in these horizontal sections 23 since they form obstacles for either one of the fluids, and force them to advance at the same velocity to within the leakage rates.

However, as described above, the velocity difference between the gas circulation and the liquid circulation directly has an influence on the gas/liquid mass transfers and advantageously has to be maintained as high as possible. This is the reason why the cleaning body should not prevent passage of the gas. For this, the cleaning body is conformed so as to let through at least partly the gas circulating inside the reaction pipe 2 while being adapted so as to be carried away by the flow of the liquid culture medium. For this purpose, said or each cleaning body 10 is made in the form of a spherical brush comprising an assembly of bristles, hairs, strands or equivalents, with a central portion bearing these bristles. Thus, in the horizontal sections 23, the emerging bristles let through the gas at the gas blanket and the immersed central portion bearing the bristles has a sufficiently large diameter in order to form an obstacle to the passage of the liquid, so that the liquid medium carries off the cleaning body 10 with itself.

In the same way, the cleaning body 10 may be made in the form of a hollow sphere in an elastomeric material, a substantial portion of the surface of which is pierced with holes which allow the gas to flow through.

Figure 4:
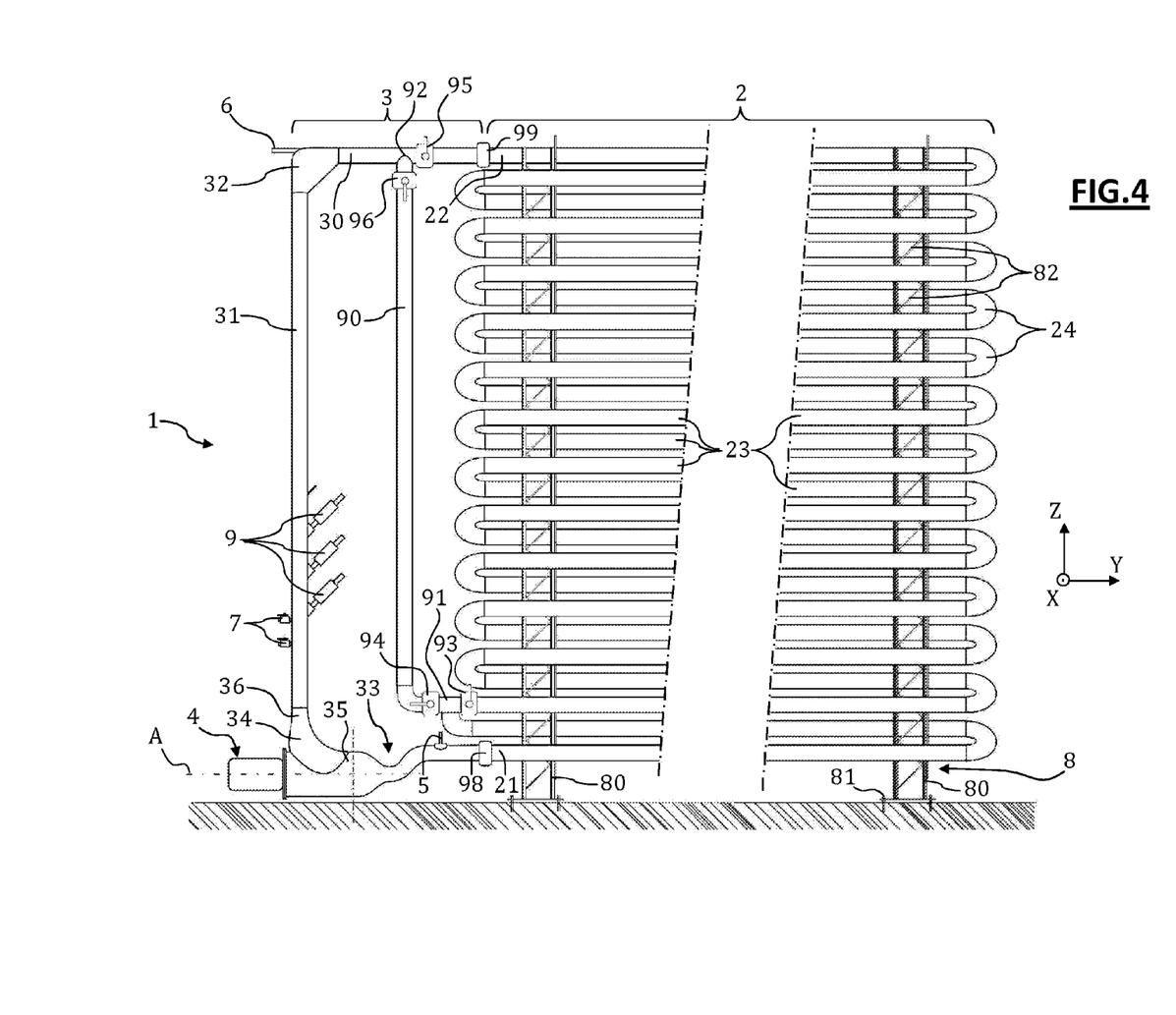
FIG. 4 is a schematic front view of another photosynthetic reactor according to the invention.

A first improvement of the reactor 1 illustrated in FIG. 4 consists of fitting out the reactor 1, as described above, with:

a short-circuit pipe 90 positioned in parallel on the return pipe 3 and connecting two connection points provided on the reactor 1, including a first connection point 91 positioned on the reaction pipe 2 and a second connection point 92 positioned on the return pipe 3 or on the reaction pipe 2 (the first connection point 91 being of course distinct from the second connection point);

two valves 93, 94 positioned on either side of said first connection point 91 with one of the valves 94 positioned on the short-circuit pipe 90; and two valves 95, 96 positioned on either side of said second connection point with one of the valves 96 positioned on the short-circuit pipe 90.

In the embodiment illustrated in FIG. 4:

the first connection point 91 is positioned on a bent section 34 or on a horizontal section 23 located above the first horizontal section (the lowermost located one) and below the last horizontal section (the uppermost located one); and the second connection point 92 is positioned on the return pipe 3, between the high end 22 of the reaction pipe 2 and the exhaust means 6 in order to allow escape of the gas in the short-circuit loop, and in particular on the upper section 30;

the valve 93 is positioned upstream from the first connection point 91 with respect to the direction of circulation of the gas, just after this first connection point 91;

the valve 94 is positioned on the short-circuit pipe 90, just after the first connection point 91;

the valve 95 is positioned between the second connection point 92 and the high end 22 of the reaction pipe 2, downstream from the second connection point 92 with respect to the direction of circulation of the gas; and the valve 96 is positioned on the short-circuit pipe 90, just before the second connection point 92.

The handling of the valves 93 to 96, which for example are of the isolation valve type with full passage, allows isolation of the portion of the reactor 1 located between both connection points 91, 92 on the side of the reaction pipe 2, and allows circulation of the gas/liquid culture medium mixture in a short-circuit loop comprising the non-isolated portion of the reactor 1 located between both connection points 91, 92 on the side of the return pipe 3 and the short-circuit pipe 90. The short-circuit pipe 90 is made in the form of a rectilinear, vertical pipe with a circular cross-section of diameter Dc equal to that of the horizontal sections 23 of the reaction pipe 2.

In the embodiment illustrated in FIG. 4, the valves 93 and 95 are closed while the valves 94 and 96 are open so that the mixture circulates in the return loop.

This improved reactor, provided with a short-circuit thus allows only a reaction subspace to be utilized, corresponding to the portion of the reaction pipe 2 positioned in the short-circuit loop, and which may represent about 1/10th of the total volume of the reaction pipe 2. In FIG. 4, this reaction subspace corresponds to the volume between the low end 21 and the first connection point 91 which corresponds to two horizontal sections 23, to be compared to the twenty-six horizontal sections of the reaction pipe 2, given as an example.

The short-circuit loop, or reduced loop, has all the functionalities of the large loop (a full circuit as in the case of the reactor of FIG. 1) since it includes:

the central section 31 with the means for injecting liquids 7 and the sensor(s) 9;

the circulation means 4;

the gas injection means 5;

the exhaust means 6; and a reaction subspace which comprises at least one horizontal section 23.

The use of such a reactor may be accomplished in the following way: after having filled the totality of the reactor 1 with sterile medium, the four valves 92 to 96 are handled so as to obtain the configuration illustrated in FIG. 4. In a first phase, the reaction subspace is inoculated and set into cultivation. In a second phase, when the concentration of micro-organisms attains a sufficient level in the reaction subspace, the four valves 92 to 96 are switched to the opposite state so that the remainder of the reaction pipe 2 is set into circulation and inoculated with the reaction subspace. One then refers to an inoculation reactor by intra-connection.

In a non-illustrated alternative embodiment of the inoculation reactor by intra-connection:

the first connection point 91 is positioned on the reaction pipe 2, on a bent section 34 or on a horizontal section 23 located above the first horizontal section and below the last horizontal section; and the second connection point 92 is also positioned on the reaction pipe 2, above the first connection point 91 (in order to short-circuit the portion of the return pipe positioned between both connection points).

In another non-illustrated alternative embodiment of the inoculation reactor by intra-connection:

the first connection point 91 is positioned on the reaction pipe 2, on a bent section 34 or a horizontal section 23 located above the first horizontal section and below the last horizontal section; and the second connection point 92 is positioned on the return pipe 3, between the gas injection means 5 and the low end 21 of the reaction pipe 2 (in order to short-circuit the portion of the return pipe positioned between its low end and the first connection point).

Figure 5:
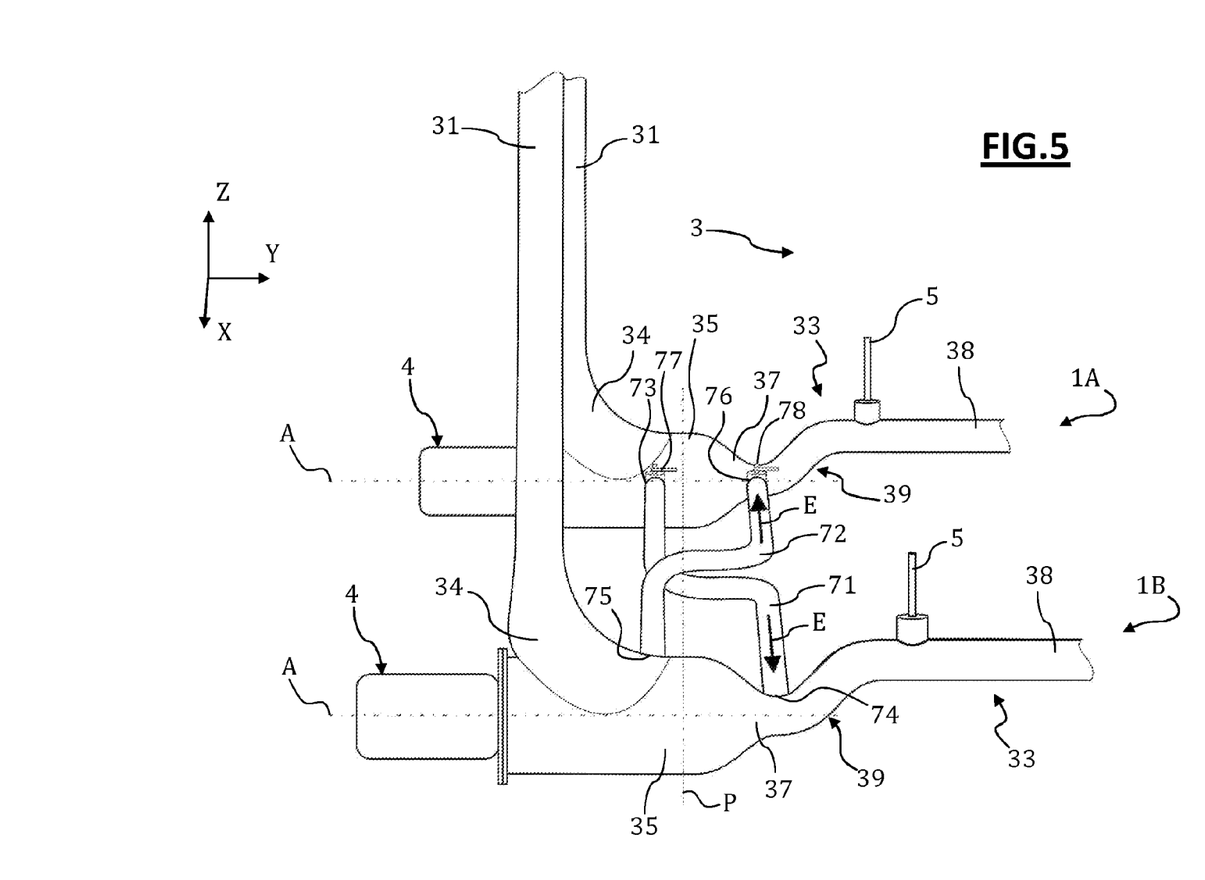
FIG. 5 is a partial schematic view of two reactors according to the invention and connected together via connection pipes.

As illustrated in FIG. 5, the invention also relates to an assembly of photosynthetic reactors comprising at least two reactors 1A, 1B according to the invention, i.e. first 1A and second 1B reactors, and comprising at least one connection pipe 71, 72 ensuring a fluidic connection between the first reactor 1A and the second reactor 1B and at least one valve 77, 78 positioned on said connection pipe 71, 72, in order to allow inoculation of one reactor by the other reactor.

In the embodiment illustrated in FIG. 5, the assembly comprises two connection pipes 71, 72 between both reactors 1A, 1B, each provided with two valves 77, 78, respectively, at the first reactor 1A, and with two other valves (non-visible and forming valves opposite to the two valves 77, 78) at the second reactor 1B, including:

a first connection pipe 71 connecting an inlet point 73 positioned on the first reactor 1A in the housing 35 upstream from the propeller (non-visible) of said first reactor 1A to an outlet point 74 positioned on the second reactor 1B downstream from the propeller (also non-visible) of said second reactor 1B; and a second connection pipe 72 connecting an inlet point 75 positioned on the second reactor 1B in the housing 35 upstream from the propeller (non-visible) of said second reactor 1B to an outlet point 76 positioned on the first reactor 1A downstream from the propeller (also non-visible) of said first reactor 1A.

The reactors 1A, 1B are assembled in parallel in order to form a consistent propipeive assembly. In order to allow inoculation of a reactor by its neighbor, for which the concentration of micro-organisms would have reached an advanced stage, the assembly provides interconnection of both of these reactors with connection pipes 71, 72, so that their respective contents are mixed.

In the embodiment illustrated in FIG. 5, the planes of rotation of both propellers coincide in a single and same vertical plane P.

Further, as visible in FIG. 5, each outlet point 74, 76 is placed at the end of the corresponding convergent tube 37 in order to benefit from a Venturi effect; said convergent tubes 37 being positioned between the respective housings 35 and the respective rectilinear portions 38.

Further, each inlet point 73, 75 is placed in the corresponding housing 35 of the propeller, preferably upstream from the corresponding plane of rotation P.

Each connection pipe 71, 72 comprises at least one valve 77, 78, allowing aseptic connection of both connection pipes 71, 72, which connect in a crossed and symmetrical way the inlet points and the outlet points of both reactors 1A, 1B to be interconnected. Each connection pipe 71, 72, may also comprise two valves, one at its inlet point and one at its outlet point.

The use of such an assembly may be accomplished in the following way: in order to proceed with the inoculation of the second reactor 1B from the first reactor 1A, already operating, and for which the concentration of micro-organisms has reached the operating level, the valves 77, 78, and their opposites are closed in a first phase and the second reactor 1B to be inoculated is filled with a sterile nutritive medium, and the circulation is then established inside the second reactor 1B. In a second phase, the valves 77, 78, and their opposites are open and a cross-exchange is established between both reactors as illustrated by the arrows E of FIG. 5.

After opening the valves 77, 78, and their opposites, the concentrations become substantially equal in both reactors 1A and 1B and it is possible to isolate them by closing the valves 77, 78, and their opposites. In order to reduce the duration of this exchange, a pump (non-visible) may be interposed on either one of the connection pipes 71, 72.

In the case when the circulation is obtained in the reactors with propulsion means other than the propeller, and when the reactors do not have any change in diameter forming a convergent tube, the Venturi effect cannot be obtained. In such a non-illustrated configuration, the interconnection between both reactors is established between the upstream side and the downstream side of both circulation means, and the propellant force establishes the exchange circulation in the direction other than the one indicated in FIG. 5.

Of course, the exemplary application mentioned above does not have any limiting nature and other details and improvements may be provided to the reactor according to the invention, without however departing from the scope of the invention, wherein other forms of reaction pipe and/or return pipe and/or circulation means may for example be achieved. Thus, the horizontal sections 23 may have a slight tilt with respect to horizontally, for example a few degrees around the horizontal direction.

The invention claimed is:

1. A photosynthetic reactor suitable for the culture of photosynthetic organisms, comprising:
    at least one photosynthetic reaction pipe in which the liquid culture medium circulates and which is provided with at least one substantially horizontal reaction section and at least partly made in a material transparent to light radiation, said reaction pipe having a low end positioned in the low portion of the reactor and a high end positioned in the high portion of the reactor above the low end;
    at least one return pipe ensuring the fluidic connection between the low end and the high end of the reaction pipe;
    at least one circulation device for circulating the liquid culture medium;
    at least one gas injector positioned in the reaction section or upstream from said reaction section with respect to the direction of the circulation of the gas, said gas injector allowing gas to be injected into the reactor; and
    at least one exhaust positioned in the high portion of the reactor and allowing the gas injected into the reactor to escape;
wherein the circulation device is positioned in the return pipe and the gas injector is positioned in the low portion of the reactor or upstream from said low portion with respect to the direction of the circulation of the gas so that the gas injected through the gas injector moves up to as far as the exhaust by circulating in the reaction pipe, in a direction of circulation from the low end to as far as the high end of the reaction pipe, so that the injected gas and the liquid culture medium establish gas/liquid two-phase flow in the substantially horizontal reaction section,
wherein circulation of the liquid culture medium is ensured by the at least one circulation device, and
wherein the reactor further comprises
    a short-circuit pipe positioned in parallel on the return pipe and connecting two connection points provided on the reactor, including a first connection point positioned on the reaction pipe and a second connection point positioned on the return pipe or on the reaction pipe;
    two valves positioned on either side of said first connection point with one of the valves positioned on the short-circuit pipe; and
    two valves positioned on either side of said second connection point with one of the valves positioned on the short-circuit pipe;
so that by handling the valves it is possible to isolate the portion of the reactor located between the first and the second connection points on the side of the reaction pipe and the gas/liquid culture medium mixture circulates in the short-circuit pipe and in the non-isolated portion of the reactor located between the first and second connection points on the side of the return pipe.

2. The reactor according to claim 1, comprising at least one liquid injector allowing injection of the liquid into the reactor, the exhaust being conformed so as to allow the excess liquid volume in the reactor to escape at the same time as the escape of the injected gas.

3. The reactor according to claim 1, wherein the circulation device is positioned in the return pipe in order to circulate the liquid culture medium in the reaction pipe of the low end up to the high end of said reaction pipe, in the same direction of circulation as the injected gas.

4. The reactor according to claim 3, wherein the gas injector is positioned in the low portion of the reactor, between the circulation device and the low end of the reaction pipe.

5. The reactor according to claim 4, wherein the return pipe has a difference in height located between the circulation means and the gas injector, said difference in height forming a difference in levels between the circulation device and the gas injector in order to avoid that the gas injected by the gas injector moves towards the circulation device.

6. The reactor according to claim 1, wherein the circulation device is positioned in the returned pipe in order to circulate the liquid culture medium in the reaction pipe of the high end to as far as the low end of said reaction pipe in a direction of circulation opposite to the direction of circulation of the injected gas.

7. The reactor according to claim 1, wherein the circulation device is a mechanical propulsion device positioned in the return pipe.

8. The reactor according to claim 7, wherein the circulation device comprises a propeller driven into rotation by a motor and wherein the return pipe has a housing with a widened cross-section, inside which said propeller is mobile in rotation.

9. The reactor according to claim 8, wherein the housing is positioned between a divergence area and a convergence area of the circulation of the liquid culture medium.

10. The reactor according to claim 1, wherein the return pipe has in the high portion a widened area and wherein the exhaust is positioned in said widened area of the return pipe.

11. The reactor according to claim 1, wherein the exhaust is positioned upstream from the circulation device with respect to the direction of circulation of the gas, in order to avoid that the gas circulates through said circulation device and is detrimental to its operation.

12. The reactor according to claim 1, comprising at least one cleaning body conformed for circulating inside the reaction and return pipes and for passing through the circulation device.

13. The reactor according to claim 12, wherein the cleaning body is conformed so as to at least partly let through the gas circulating inside the reaction pipe while being adapted so as to be driven by the circulation of the liquid culture medium.

14. The reactor according to claim 13, wherein the cleaning body is made in the form of a brush comprising an assembly of bristles, hairs, strands or equivalents, or in the form of a hollow sphere in elastomeric material, at least one portion of the surface of which is pierced with holes.

15. An assembly of photosynthetic reactors adapted for cultivating photosynthetic microorganisms comprising at least two reactors according to claim 1, a first and a second reactors, and comprising at least one connection pipe ensuring a fluidic connection between the first reactor and the second reactor and at least one valve positioned on said connection pipe.

16. The assembly according to claim 15, comprising two connection pipes between both reactors, each provided with at least one valve, including:
   a first connection pipe connecting an inlet point positioned on the first reactor upstream from the circulation device of said first reactor to an outlet point positioned on the second reactor downstream from the circulation device of said second reactor; and
   a second connection pipe connecting an inlet point positioned on the second reactor upstream from the circulation device of said second reactor to an outlet point positioned on the first reactor downstream from the circulation device of said first reactor.

17. The assembly according to claim 15, comprising a pump interposed on either one of the connection pipes.

18. The reactor according to claim 1, wherein the reaction pipe comprises several substantially horizontal reaction sections, said reaction sections being successively connected through bent sections, the horizontal sections and the bent sections being connected in series at intervals so that the reaction pipe has the shape of a continuous conduit between its low end and its high end.

19. A method for cultivating photosynthetic microorganisms comprising the following steps:
   providing a reactor according to claim 1;
   injecting a liquid culture medium into the reactor according to a controlled flow rate;
   injecting a gas into the reactor according to a controlled flow rate with the gas injector so that the gas injected through the gas injector moves up to as far as the exhaust by circulating in the reaction pipe, in a direction of circulation from the low end to as far as the high end of the reaction pipe;
   circulating the liquid culture medium with the circulation device;
   controlling the circulation device and the gas injector in order to establish in the reaction section gas/liquid two-phase flow conditions of the laminated flow or slug flow or elongated bubble flow type;
   and wherein the circulation of the liquid is not driven by a gas-lift in order that the gas-liquid transfer does not occur inside a vertical bubble column of a gas-lift but along at least one substantially horizontal reaction section in which the flow is subject to conditions of the horizontal two-phase type.

20. The method according to claim 19, wherein the control step comprises a step for controlling the circulation rate of the liquid in the reaction pipe between 0.1 and 0.2 m/s in order to establish two-phase flow conditions of the laminated flow type.

21. The method according to claim 19, wherein the control step comprises a step for controlling the circulation rate of the liquid in the reaction pipe between 0.2 and 1 m/s in order to establish two-phase flow conditions of the slug or elongated bubble flow type.

22. The method according to claim 19, wherein the control step comprises a step for controlling the circulation rate of the gas between 0.5 and 0.8 m/s.

23. The method according to claim 19, wherein the circulation device comprises a propeller driven into rotation by a motor and wherein the speed of rotation of the propeller is less than 100 revolutions per minute.

24. The method according to claim 19, wherein the reaction pipe comprises several substantially horizontal reaction sections, said reaction sections being successively connected through bent sections, the horizontal sections and the bent sections being connected in series at intervals so that the reaction pipe has the shape of a continuous conduit between its low end and its high end, and
   wherein the control step establish gas-liquid exchanges through an interface formed at the free surface of the liquid in the substantially horizontal reaction sections of the reaction pipe in which the circulation of the gas and of the liquid is substantially established horizontally according to gas/liquid two-phase flow conditions of the stratified or slug or elongated bubble flow.

* * * * *